United States Patent [19]

Danninger et al.

[11] 4,168,205

[45] Sep. 18, 1979

[54] METHOD FOR THE DETERMINATION OF SUBSTRATES OR ENZYME ACTIVITIES

[75] Inventors: Josef Danninger, Grafelfing; Ulfert Deneke, Peissenberg; Gunter Lang; Gerhard Michal, both of Tutzing; Peter Roeschlau, Seeshaupt, all of Fed. Rep. of Germany

[73] Assignee: Boehringer Mannheim GmbH, Mannheim-Waldhof, Fed. Rep. of Germany

[21] Appl. No.: 792,073

[22] Filed: Apr. 28, 1977

[30] Foreign Application Priority Data

Jun. 9, 1976 [DE] Fed. Rep. of Germany ....... 2625834

[51] Int. Cl.$^2$ ............................................ G01N 33/16
[52] U.S. Cl. ......................................... 435/10; 435/14; 435/25; 435/28
[58] Field of Search ................. 195/103.5 C, 103.5 R, 195/99

[56] References Cited

U.S. PATENT DOCUMENTS

| 3,721,607 | 3/1973 | Gruber et al. ................. 195/103.5 C |
| 3,791,988 | 2/1974 | Josef et al. .................... 195/103.5 C |
| 3,992,158 | 11/1976 | Przybylowicz et al. ...... 195/103.5 R |

OTHER PUBLICATIONS

Gerwin et al., Journal of Biological Chemistry, vol. 249, No. 7, pp. 2005–2008, Apr. 1974.
Bailey, The Standard Cyclopedia of Horticulture, pp. 909, 910, 2860 and 2861 (1943).

*Primary Examiner*—Lionel M. Shapiro
*Attorney, Agent, or Firm*—Sprung, Felfe, Horn, Lynch & Kramer

[57] ABSTRACT

In a process for the determination of substrates or enzyme activities in a test batch, utilizing a conventional redox reaction as a measurement reaction, the improvement comprising carrying out the process in the presence of ascorbate oxidase; the addition of ascorbate oxidase substantially eliminates the interfering effect of ascorbic acid frequently found in the test sample.

22 Claims, 2 Drawing Figures

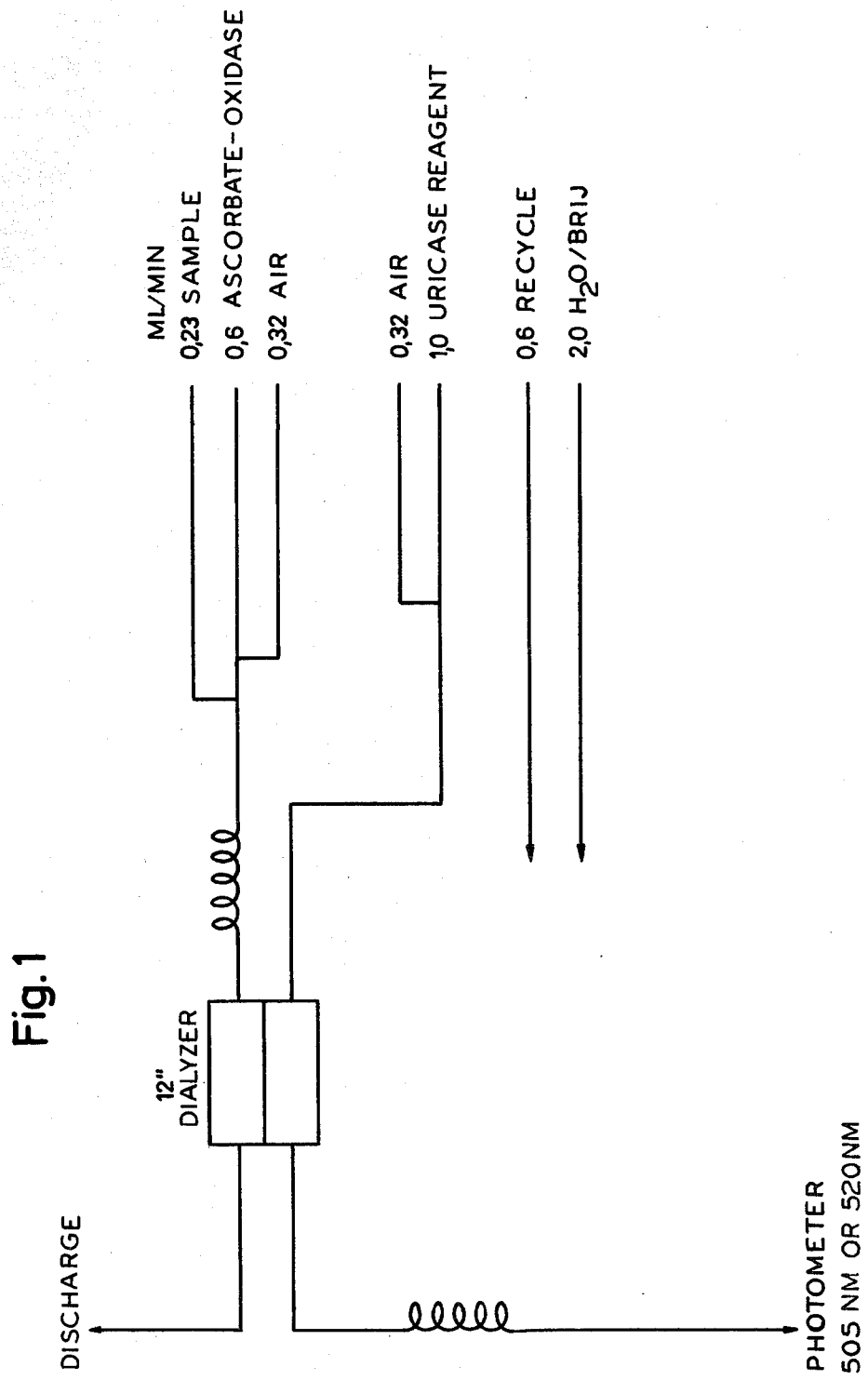

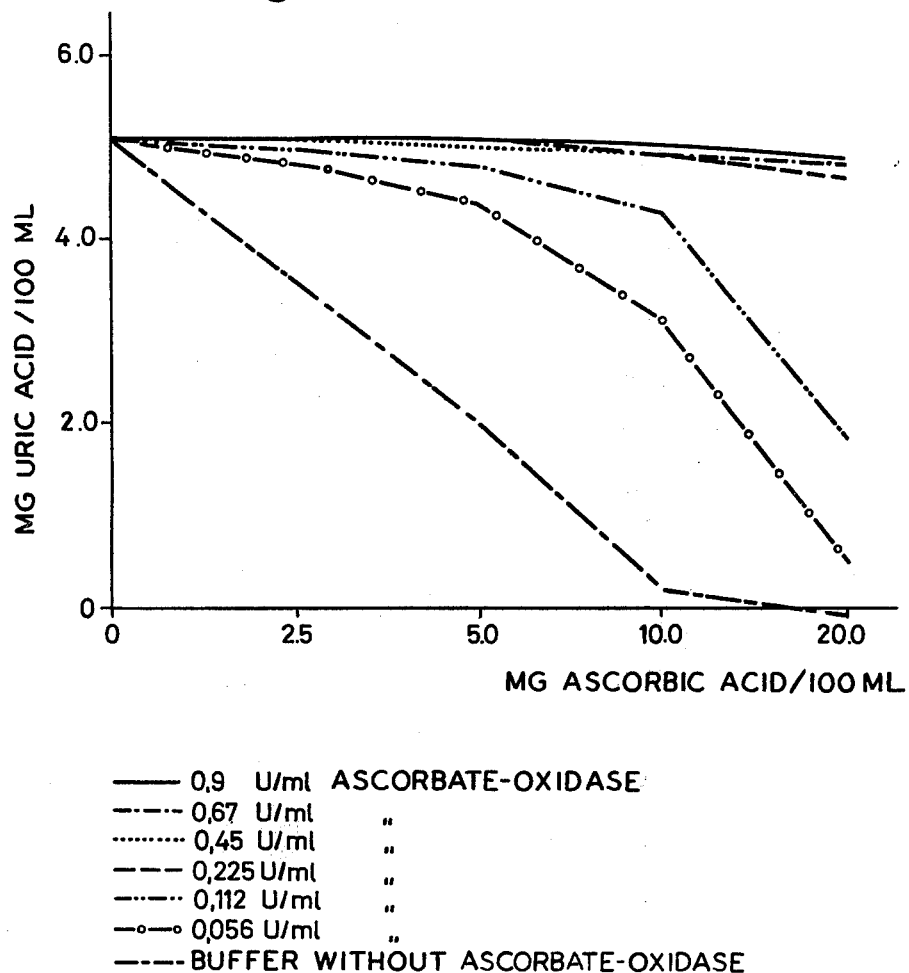

METHOD FOR THE DETERMINATION OF SUBSTRATES OR ENZYME ACTIVITIES

The invention relates to the determination of enzyme activity or substrates. More specifically, the present invention is concerned with a process for the determination of substrates or enzyme activities with the use of a redox reaction as measurement reaction and is also concerned with a reagent for carrying out this process.

In clinical and pharmaceutical chemistry, biochemistry and foodstuff chemistry, redox reactions are of great interest for the determination of ensyme or substrate concentrations. These reactions can be evaluated by photometric measurements. If, in addition to the redox components of interest, the test system contains other reducing substances, disturbances can occur. Ascorbic acid is found especially frequently in sample material. Since it is a strong reducing agent, it gives rise to disturbances when investigating pharmaceuticals or physiological fluids, such as serum or urine, ascorbic acid-containing plant juices or other foodstuffs which contain ascorbic acid or to which ascorbic acid has been added. Thus, for example, it is known that the following reactions are disturbed by ascorbic acid:

(A) reactions in which hydrogen peroxide and a hydrogen donor are reacted with peroxidase (POD) are disturbed by the reaction:

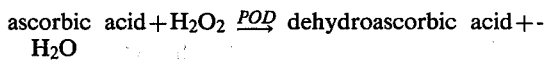
ascorbic acid + $H_2O_2$ $\xrightarrow{POD}$ dehydroascorbic acid + $H_2O$ (B) reactions in which tetrazolium salts are reduced with reducing agents to give formazanes are disturbed by the reaction:

ascorbic acid + tetrazolium salt → formazane + dehydroascorbic acid (C) reactions in which phenols are oxidatively coupled with nucleophilic reagents are disturbed because ascorbic acid gives rise to side reactions, which have not yet been elucidated, so that non-uniform coupling products are formed, the absorption behavior of which deviates in normal and ultra-violet light from the coupling products normally formed.

Conventional oxidation methods are, as a rule, unsuitable for the removal of ascorbic acid from the sample material. Oxidation agents also attack and destroy substrates and enzymes. Their reduction products, which are mostly di- and trivalent metal ions, frequently inhibit the enzymes used for the indicator reaction. The destruction of ascorbic acid in the presence of oxygen necessitates the use of strongly alkaline media, for example a 25% aqueous solution of sodium hydroxide. This also leads to the destruction of substrates and enzymes.

Therefore, the art faced the problem of providing a process for the determination of substrates or enzyme activities, with the use of a redox reaction as measurement reaction, which is not subject to disturbance by ascorbic acid.

The present invention solves this problem by adding ascorbate oxidase to the reaction batch.

Ascorbate oxidase catalyses the reaction:

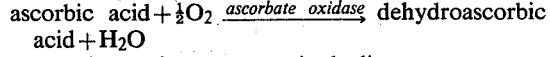
ascorbic acid + $\frac{1}{2}O_2$ $\xrightarrow{ascorbate\ oxidase}$ dehydroascorbic acid + $H_2O$ According to the statements in the literature concerning ascorbic acid oxidase, it was to have been expected that this enzyme could not be employed for the purpose according to the present invention. Thus, all previously obtained enzyme preparations produce hydrogen peroxide in a side reaction. At the same time, ascorbate oxidase undergoes a very rapid inactivation which is ascribed to the simultaneously formed hydrogen peroxide (Biochemical Copper Proceedings Symposium Harriman, New York 1965, pp. 305–337). This also applies to the most highly purified preparations which, in the ultracentrifuge and by electrophoresis, no longer show the presence of any impurities (Biochem. 4, 1362–1370/1965). The inactivation of the reaction is ascribed to the formation of hydrogen peroxide (Biochem. Biophys. Acta 56, 427 to 439/1962). According to the calculations of the latter authors, 1 U ascorbate oxidase in 1 mMol/liter ascorbic acid solution can produce $0.7 \times 10^{-2}$ mMol/liter of hydrogen peroxide, such ascorbate concentrations being frequently present in sample solutions. The hydrogen peroxide formed is certainly available for enzymatic reactions, which has been demonstrated in the case of, for example, catalase.

In the system:

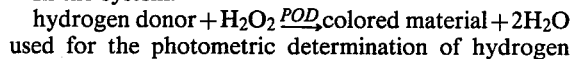
hydrogen donor + $H_2O_2$ $\xrightarrow{POD}$ colored material + $2H_2O$ used for the photometric determination of hydrogen peroxide, at a molar extinction coefficient of about 20 $cm^2/\mu Mol$, it brings about an extinction difference of 0.14. Since the measurement range of normal photometric reactions extends from about 0.01–1.00, this gives rise to an unacceptable error. In the same way, reactions are disturbed in which, instead of hydrogen peroxide, use is made of organic hydroperoxides and instead of POD, use is made of haemoglobin or of other oxidation catalysts.

However, apart from these errors brought about by hydrogen peroxide, it is known from the above last-mentioned literature reference that the reaction of the ascorbic acid already comes to a stop long before its complete removal.

This would be especially serious in the case of all those redox reactions in which hydrogen peroxide is formed since this hydrogen peroxide would certainly, on the one hand, further accelerate the inactivation of the enzyme and, on the other hand, the new formation of hydrogen peroxide by the ascorbate oxidase itself leads to completely unpredictable phenomena. Therefore, it is most surprising that, contrary to expectations, it is possible completely to remove the disturbances brought about by the presence of ascorbate by the addition of ascorbate oxidase, without other disturbances arising which would again nullify the advantage of the ascorbate removal.

The process according to the present invention is preferably used in the case of enzymatic reactions, especially those in which hydrogen peroxide is formed and thus in the case of reactions which are catalyzed by oxidases, such as glucose oxidase, uricase, cholesterol oxidase and the like, as well as in the case of reactions in which tetrazolium salts are reduced and in the case of reactions in which phenols are oxidatively coupled with nucleophilic reagents. The amount of ascorbate oxidase added depends upon the amount of ascorbic acid to be expected in the sample. As a rule, 0.002 to 100 U ascorbate oxidase/ml. and preferably 0.01 to 30 U/ml., are added to the test batch. The pH value of the reaction depends, in the first place, upon the pH value which is necessary for the other participating enzyme or enzymes. pH values of from 4.0 to 8.5 are usually appropriate for the process of the present invention. According to the invention, it is especially preferred to use an ascorbate oxidase obtained from small marrows (*Curcurbita pepo medullosa*). However, ascorbate oxidase of other origin can also be used.

The present invention also provides a reagent for the determination of substrates or enzyme activities, comprising a system for the determination of a substrate or enzyme with a redox reaction as measurement reaction, the reagent additionally containing ascorbate oxidase.

Preferred reagents of this type contain, when glucose is the substrate to be determined, peroxidase, glucose oxidase, o-dianisidine or azino-di-3-ethylbenzylthiazoline-6-sulphonate, together with buffer, or hexokinase (HK), glucose-6-phosphate dehydrogenase (G6P-DH), diaphorase, nicotinamide-adenine-dinucleotide phosphate (NADP), a tetrazolium salt, such as 3-(4-iodophenyl)-2-(4-nitrophenyl)-5-phenyl-2H-tetrazolium chloride (INT) and buffer. When uric acid is the substrate to be determined, the system preferably comprises peroxidase, uricase, a phenol, such as 2,4-dichlorophenol, aminoantipyrine and buffer. In the case of the determination of glutamate, the system preferably comprises glutamate dehydrogenase (G1DH), diaphorase, nicotinamide-adenine-dinucleotide (NAD), INT and buffer. For the determination of tyrosine, the system preferably comprises tyrosinase, 3-methyl-6-potassium sulphonyl-benzthiazolone-2-hydrazone and for the determination of pyrocatechol, the system preferably comprises diphenol oxidase and 3-methyl-6-potassium sulphonyl-benzthiazolone-2-hydrazone, in each case together with a buffer. All these systems for the determination of substrates are known. However, there can also be used instead other known systems for the determination of substrates or enzymes within the scope of the reagent according to the present invention.

The present invention is also of special importance for use in the field of rapid diagnostics. As a rule, such rapid diagnostics contain the various reagents needed for carrying out the process either impregnated in an absorbent carrier or applied, together with an appropriate binding agent, to a carrier film. A preferred embodimental form is the addition of the ascorbate oxidase to the mixture of the other reagents, with subsequent impregnation into an absorbent carrier. In this way, there can be obtained test papers which are practically not disturbed, for example, by ascorbic acid when used for the detection of glucose in urine (for example, according to German Pat. No. 23 38 932) or of blood in urine (for example, according to German Pat. Nos. 2,460,903 or 2,235,152) or of blood in faeces. That the ascorbate oxidase in test papers for the detection of blood in urine remains capable of functioning and is also storage-stable is most surprising because these test papers contain large amounts of organic hydroperoxides which, similarly to hydrogen peroxide, would have been expected to cause an inactivation of the ascorbate oxidase.

The ascorbate oxidase can, however, also be applied to a separate carrier which is then combined with the carrier for the other reagents, for example, laid thereover, stuck thereto or jointly sealed in between appropriate materials. In this case, an especially preferred carrier for the ascorbate oxidase is a so-called water-soluble paper (for example, according to German Pat. No. 2,436,598) which allows the color reaction to be observed especially well on the carrier paper containing the other reagents. This embodiment is especially advantageous when, in the reagent combination, substances are present which are incompatible with the ascorbate oxidase, for example strongly acidic reagents such as are used in processes for the determination of urobilinogen, bilirubin and nitrite.

In the case of the above embodiments, there can be used up to 5000 U and preferably up to 2000 U ascorbate oxidase per ml. impregnation solution for the preparation of the reagent. In general, less than 1 U/ml. will not ensure the desired effect.

Furthermore, separate zones of a carrier material can also be impregnated with the ascorbate oxidase or the other test reagents. In this case, the carrier is preferably brought into contact with the solution to be investigated in such a manner that the solution first comes into contact with the ascorbate oxidase-containing zone and from there is drawn into the zone which contains the other test reagents.

According to a further embodiment, the ascorbate oxidase can be bound to an insoluble carrier material by methods known for enzyme fixing, methods of this type being described, for example, in German Pat. Nos. 1,768,512; 2,128,743; 2,260,185; 2,260,184; 2,426,988; 26 03 158 and 1,915,970.

The process according to the present invention is preferably used for the determination of glucose with peroxidase, glucose oxidase and o-dianisidine or 2,2′-azino-di-3-ethylbenzthiazoline-6-sulphonate (ABTS), for the determination of glucose by the hexokinase/-glucose-6-phosphate dehydrogenase method, for the detection of uric acid by means of phenol, aminoantipyrine, peroxidase and uricase, for the determination of tyrosine or pyrocatechol by means of SMBTH (4-methyl-6-potassium sulphonylbenzthiazolone-2-hydrazone) and tyrosinase or diphenol oxidase, respectively.

The following Examples are given for the purpose of illustrating the present invention:

EXAMPLE 1

Determination of glucose with o-dianisidine, peroxidase (POD) and glucose oxidase (GOD), measured in a photometer; wavelength 432 nm; measurement temperature: 25° C.

| cuvette No. | 1 | 2 | 3 | 4 | 5 |
| --- | --- | --- | --- | --- | --- |
| phosphate buffer pH 7.01 M | 2.5 | 2.5 | 2.5 | 2.5 | 2.5 |
| o-dianisidine 5 mg./ml. | 0.1 | 0.1 | 0.1 | 0.1 | 0.1 |
| POD, 180 U/ml. | 0.05 | 0.05 | 0.05 | 0.05 | 0.05 |
| glucose solution 1 mg./ml. | 0.03 | 0.03 | 0.03 | 0.03 | 0.03 |
| ascorbic acid solution 10 mM | — | 0.1 | 0.01 | 0.1 | 0.01 |
| water | 0.12 | 0.02 | 0.11 | — | 0.09 |
| ascorbate oxidase 500 U/ml. | — | — | — | 0.02 | 0.02 |
| incubate for 1 min at 25° C. read off $E_1$ then start with | | | | | |
| GOD 70 U/ml | 0.1 | 0.1 | 0.1 | 0.1 | 0.1 |
| incubate for 30 min at 25° C. read off $E_2$ calculate $\Delta E$ from $E_2-E_1$ | | | | | |
| $\Delta E$ | 0.541 | 0.010 | 0.316 | 0.540 | 0.543 |

Cuvette 1 corresponds to an undisturbed measurement (no ascorbic acid). Cuvettes 2 and 3 show that 1 or 0.1 μMol ascorbate practically completely inhibit or 41.5% inhibit the test and cuvettes 4 and 5 show the complete destruction of these ascorbate concentrations by the addition, in each case, of 10 U ascorbate oxidase.

EXAMPLE 2

Detection of glucose with 2,2'-azino-di-(3-ethyl-benzthiazoline-6-sulphonate) (ABTS), POD and GOD in a photometer; wavelength: 432 nm; measurement temperature: 25° C.

| cuvette No. | 1 | 2 | 3 | 4 | 5 |
|---|---|---|---|---|---|
| phosphate buffer pH 5.6 0.1M | 2.75 | 2.75 | 2.75 | 2.75 | 2.75 |
| ABTS 50 mM | 0.05 | 0.05 | 0.05 | 0.05 | 0.05 |
| POD 250 U/ml. | 0.02 | 0.02 | 0.02 | 0.02 | 0.02 |
| glucose solution 0.1 mg./ml. | 0.1 | 0.1 | 0.1 | 0.1 | 0.1 |
| ascorbic acid solution 1mM | — | 0.1 | 0.01 | 0.1 | 0.01 |
| water | 0.12 | 0.02 | 0.11 | — | 0.09 |
| ascorbate oxidase 500 U/ml. | — | — | — | 0.02 | 0.02 |
| incubate for 1 min. at 25° C., read off $E_1$, start with | | | | | |
| GOD 70 U/ml. | 0.1 | 0.1 | 0.1 | 0.1 | 0.1 |
| incubate for 30 min. at 25° read off $E_2$, calculate $\Delta E$ from $E_2-E_1$ | | | | | |
| $\Delta E$ | 0.505 | 0.000 | 0.40 | 0.502 | 0.504 |

Cuvette 1 corresponds to an undisturbed measurement (no ascorbate). Cuvettes 2 and 3 show that 0.1 or 0.01 µMol ascorbate completely inhibit or 21% inhibit the test and cuvettes 4 and 5 show the complete destruction of these ascorbate concentrations by the addition, in each case, of 10 U ascorbate oxidase.

EXAMPLE 3

Detection of uric acid by means of phenol, aminoantipyrine, POD and uricase in an automatic analyzer (AutoAnalyser).

Test principle

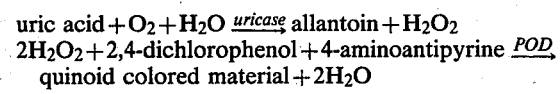

uric acid + $O_2$ + $H_2O$ $\xrightarrow{uricase}$ allantoin + $H_2O_2$
$2H_2O_2$ + 2,4-dichlorophenol + 4-aminoantipyrine $\xrightarrow{POD}$ quinoid colored material + $2H_2O$

Preparation of the solutions

1. Ascorbate oxidase reagent

In 600 ml. double distilled water, there is dissolved the content of flask 1 and 0.3 ml. Brij-35 is added. The solution can be stored in a dark bottle at about 4° C. for four weeks and at about 25° C. one week.

2. Uricase reagent

In 800 ml. double distilled water, there is dissolved the content of flask 2 and 2.0 ml. Brij-35 are added. The solution can be stored in a dark bottle at about 4° C. for four weeks and at about 25° C. for one week.

Concentrations of the solutions 1. 50 mM phosphate buffer, pH 5.6 ascorbate oxidase-
   ≧in the amounts which can be seen from FIG. 2 of the accompanying drawings.
2. 31 mM tris-(hydroxymethyl)-aminomethane/citric acid, pH 8.9
   uricase≧0.08 U/ml.
   POD≧0.015 U/ml.
   3.0 mM 2,4-dichlorophenol
   4.0 mM 4-aminoantipyrine For the carrying out of the determination, the flow systems of the automatic device is assembled according to the flow diagram illustrated in FIG. 1 of the accompanying drawings.

FIG. 2 of the accompanying drawings summarizes, in graphic form, the experimental results obtained.

EXAMPLE 4

Detection of glucose with HK/G6P-DH, NADP, INT and diaphrorase in a photometer; measurement wavelength: 492 nm; incubation temperature: 25° C.

| cuvette No. | 1 | 2 | 3 |
|---|---|---|---|
| phosphate buffer, pH 7.5 0.1M | 1.7 | 1.7 | 1.7 |
| NADP/INT each 1 mg./ml. | 0.1 | 0.1 | 0.1 |
| diaphorase 5 U/ml. | 0.1 | 0.1 | 0.1 |
| glucose solution 0.05 mg./ml. | 0.1 | 0.1 | 0.1 |
| ascorbate solution 10 mM | — | 0.01 | 0.01 |
| ascorbate oxidase 35 U/ml. | — | — | 0.03 |
| water | 0.04 | 0.03 | — |
| incubate for 3 min. at 25° C., read off $E_1$, start with | | | |
| HK/G6P-DH solution each 56 U/ml. | 0.05 | 0.05 | 0.05 |
| incubate for 15 min., read off $E_2$, calculate $\Delta E$ from $E_2-E_1$ | | | |
| $\Delta E$ | 0.234 | 0.307 | 0.230 |

Cuvette 1 corresponds to an undisturbed measurement, cuvette 2 shows that 0.01 µMol ascorbate gives a test result which is 34% too high and cuvette 3 shows that 1 U ascorbate oxidase completely overcomes this disturbance.

EXAMPLE 5

Determination of glutamate by means of G1DH, NAD/INT/diaphorase in a photometer; measurement wavelength 492 nm; temperature 25° C.

| cuvette No. | 1 | 2 | 3 | 4 | 5 |
|---|---|---|---|---|---|
| phosphate buffer, pH 5.6, 0.01 mM | 1.30 | 1.20 | 1.29 | 1.18 | 1.27 |
| glutamate solution 0.2 mg./ml. | 0.1 | 0.1 | 0.1 | 0.1 | 0.1 |
| ascorbate solution 5 mM | — | 0.1 | 0.01 | 0.1 | 0.01 |
| ascorbate oxidase 100 U/ml. | — | — | — | 0.02 | 0.02 |
| incubate for 3 min. at 25° C., then pipette into the individual cuvettes | | | | | |
| 0.2 M TRA, 0.05 M potassium phosphate buffer, pH 8.6 with 1.5% Triton-X-100 | 1.0 | 1.0 | 1.0 | 1.0 | 1.0 |
| NAD solution 5 mg/ml. | 0.2 | 0.2 | 0.2 | 0.2 | 0.2 |
| diaphorase solution 10 U/ml. | 0.05 | 0.05 | 0.05 | 0.05 | 0.05 |
| G1DH 1000 U/ml. | 0.05 | 0.05 | 0.05 | 0.05 | 0.05 |
| read off $E_1$, start reaction with | | | | | |
| INT solution, 2 mg/ml. | 0.05 | 0.05 | 0.05 | 0.05 | 0.05 |
| incubate for 15 min. at 25° C., read off $E_2$, calculate $\Delta E$ from $E_2-E_1$ | | | | | |
| $\Delta E$ | 0.184 | 1.560 | 0.380 | 0.186 | 0.182 |

Cuvette 1 corresponds to an undisturbed measurement, cuvettes 2 and 3 show that 0.5 or 0.05 µMol ascorbate give test results which are 700 or 100% too high and cuvettes 4 and 5 show the complete removal of this disturbance by 2 U ascorbate oxidase.

EXAMPLE 6

Determination of tyrosine with 3-methyl-6-potassium sulphonyl-benzthiazolone-2-hydrazone (SMBTH) and tyrosinase in a photometer; measurement wavelength 492 nm; measurement temperature 25° C.

| cuvette No. | 1 | 2 | 3 |
| --- | --- | --- | --- |
| phosphate buffer, pH 5.2 0.25 M | 2.77 | 2.77 | 2.77 |
| SMBTH 0.1M | 0.05 | 0.05 | 0.05 |
| ascorbic acid solution 10 mM | — | 0.1 | 0.1 |
| water | 0.12 | 0.02 | — |
| ascorbate oxidase 500 U/ml. | — | — | 0.02 |
| tyrosinase 60 U/ml. | 0.05 | 0.05 | 0.05 |
| incubate for 1 min. at 25° C., read off $E_1$, start with | | | |
| tyrosine 2 mM | 0.05 | 0.05 | 0.05 |
| incubate for 1 hr. at 25° C., read off $E_2$, calculate $\Delta E$ from $E_2 - E_1$ | | | |
| $\Delta E$ | 1.118 | 0.728 | 1.100 |

Cuvette 1 corresponds to an undisturbed measurement, in cuvette 2, 1 μMol ascorbate lowers the theoretical value by 35% and in cuvette 3 this disturbance is completely removed by 10 U ascorbate oxidase.

EXAMPLE 7

Determination of pyrocatechol with SMBTH and diphenol oxidase.

| cuvette No. | 1 | 2 | 3 |
| --- | --- | --- | --- |
| phosphate buffer, 0.25 M pH 5.2 | 2.80 | 2.70 | 2.68 |
| SMBTH 0.1 M | 0.05 | 0.05 | 0.05 |
| pyrocatechol 0.5 mM | 0.10 | 0.10 | 0.10 |
| ascorbate solution 20 mM | — | 0.1 | 0.1 |
| ascorbate oxidase 500 U/ml. | — | — | 0.02 |
| incubate for 1 min. at 25° C., read off $E_1$, start with | | | |
| diphenol oxidase 200 U/ml. | 0.05 | 0.05 | 0.05 |
| incubate for 17 min. at 25° C., read off $E_2$, calculate $\Delta E$ from $E_2 - E_1$ | | | |
| $\Delta E$ | 0.890 | 0.485 | 0.896 |

Cuvette 1 corresponds to an undisturbed measurement, in cuvette 2, 2 μMol ascorbate lowers the theoretical value by 47% and in cuvette 3 this disturbance is completely removed by 10 U ascorbate oxidase.

EXAMPLE 8

Test paper for the detection of glucose in the urine.

Filter paper is impregnated with a solution of the following composition and dried at 50° C.:

| 1.2 M citrate buffer pH 5 | 50.0 ml. |
| --- | --- |
| 9-(γ-dimethylaminopropyl)-6-chloro-3-aminocarbazole dihydrochloride | 0.75 g. |
| glucose oxidase (10$^4$ U/mg.) | 0.25 g. |
| peroxidase (63 U/mg.) | 0.05 g. |
| ascorbate oxidase (100 U/mg.) | 1.00 g. |
| water | 100.0 ml. |

The test paper reacts with glucose-containing urines with red-orange to black-red colour shades. After a reaction time of 2 minutes, urines with the same glucose contents but also with ascorbic acid contents of up to 150 mg./dl. give practically the same reaction colors. With test papers of analogous composition but without ascorbate oxidase, depending upon the glucose content, the reaction colours are weakened or completely suppressed in the case of ascorbic acid concentrations above 50 mg./dl.

EXAMPLE 9

Test paper for the detection of blood in the urine.

Filter paper is successively impregnated with the following solutions and dried at 40° C.

| Solution 1 | |
| --- | --- |
| 1.2M citrate buffer pH 5.25 | 35.0 ml. |
| ethylenediamine-tetraacetic acid disodium salt | 0.1 g. |
| dioctyl sodium sulphosuccinate | 0.5 g. |
| 2,5-dimethylhexane-2,5-dihydro-peroxide (about 70%) | 1.6 g. |
| phosphoric acid trimorpholide | 12.7 g. |
| ascorbate oxidase (100 U/mg.) | 0.3 g. |
| methanol | 30.0 ml. |
| water | ad 100.0 ml. |

| Solution 2 | |
| --- | --- |
| 3,3',5,5'-tetramethylbenzidine | 0.3 g. |
| phenanthridine | 0.2 g. |
| toluene/petroleum ether (30:70 v/v) | ad 100.0 ml. |

With this test paper, there can be detected the presence of 5 erythrocytes/mm$^3$ in the urine, even in the presence of 30 to 50 mg. ascorbic acid/100 ml. With a test paper of the same composition but without ascorbate oxidase this detection is no longer possible even in the presence of only 10–20 mg. ascorbic acid/100 ml.

EXAMPLE 10

Test paper A

Test paper as in Example 9 but without ascorbate oxidase.

Test paper B

Water-soluble carboxymethylcellulose paper (weight 60 g./m$^2$) is impregnated with a solution of 20% glacial acetic acid in methanol for the purpose of neutralization and then dried. Thereafter, it is sprayed with an aqueous solution of ascorbate oxidase (10$^3$ U/ml.) and dried immediately.

Test paper B is laid upon test paper A and both are sealed in together between a polyester film and a nylon mesh. The urine to be investigated is dropped on to the test strips so produced.

The results obtained are analogous to those of Example 9.

EXAMPLE 11

Test paper for the detection of blood in faeces.

Filter paper is successively impregnated with the following solutions and dried at 40° C.

| Solution 1 | |
| --- | --- |
| 1.2 M citrate buffer, pH 5.25 | 10 ml. |
| ascorbate oxidase 100 U/mg. | 0.3 g. |
| water | ad 100.0 ml. |

| Solution 2 | |
| --- | --- |
| gum guaiac | 3 g. |
| toluene | ad 100.0 ml. |

The solution is filtered and the filtrate is used for the impregnation.

The test paper obtained is coated with faeces. If, on the rear side, there is dropped on a 3% aqueous solution of hydrogen peroxide, then a blue coloration is obtained when the faeces contain about 2% blood. This coloration also occurs in the case of ascorbic acid-containing faeces (about 15 mg./100 g.), whereas it does not occur when the test paper does not contain ascorbate oxidase.

It will be understood that the specification and examples are illustrative but not limitative of the present invention and that other embodiments within the spirit and scope of the invention will suggest themselves to those skilled in the art.

What is claimed is:

1. In a process for the determination of substrates or enzyme activities in a test batch, utilizing a redox reaction as a measurement reaction, the improvement comprising carrying out the process in the presence of ascorbate oxidase obtained from small marrow (*Curcurbita pepo medullosa*).

2. Process as claimed in claim 1 wherein 0.002 to 100 U ascorbate oxidase/ml. test batch are used.

3. Process as claimed in claim 2 wherein 0.01 to 30 U ascorbate oxidase/ml. test batch are used.

4. Process as claimed in claim 1 wherein the ascorbate oxidase is used together with an enzyme forming hydrogen peroxide.

5. Process as claimed in claim 1 wherein the ascorbate oxidase is used together with a tetrazolium salt.

6. Process as claimed in claim 1 wherein the ascorbate oxidase is used together with a phenol capable of being coupled oxidatively with a nucleophilic reagent.

7. Process as claimed in claim 1 wherein it is carried out at a pH value of from 4.0 to 8.5.

8. Process as claimed in claim 7 wherein there is used an ascorbate oxidase obtained from small marrows (*Curcurbita pepo medullosa*).

9. Reagent for the enzymatic determination of substrates or enzyme activities, comprising a system for the determination of a substrate or enzyme with a redox reaction as measurement reaction, wherein ascorbate oxidase obtained from small marrow (*Curcurbita pepo medullosa*) is additionally present.

10. Reagent as claimed in claim 9 wherein the system for the determination of a substrate serves for the determination of glucose and comprises peroxidase, glucose oxidase, o-dianisidine or 2-azino-di-3-ethyl-benzthiazoline-6-sulphonate and buffer.

11. Reagent as claimed in claim 9 wherein the system for the determination of a substrate serves for the determination of uric acid and comprises peroxidase, uricase, a phenol, aminoantipyrine and buffer.

12. Reagent as claimed in claim 11 wherein the phenol is 2,4-dichlorophenol.

13. Reagent as claimed in claim 9 wherein the system for the determination of a substrate serves for the determination of glucose and comprises hexokinase, glucose-6-phosphate dehydrogenase, nicotinamide-adenine-dinucleotide phosphate, diaphorase, a tetrazolium salt and buffer.

14. Reagent as claimed in claim 9 wherein the system for the determination of a substrate serves for the determination of glutamate and comprises glutamate dehydrogenase, diaphorase, nicotinamide-adenine-dinucleotide, a tetrazolium salt and buffer.

15. Reagent as claimed in claim 9 wherein the system for the determination of a substrate serves for the determination of tyrosine and comprises tyrosinase, 3-methyl-6-potassium sulphonyl-benzthiazolone-2-hydrazone and buffer.

16. Reagent as claimed in claim 9 wherein the system for the determination of a substrate serves for the determination of pyrocatechol and comprises diphenol oxidase, 3-methyl-6-potassium sulphonyl-benzthiazolone-2-hydrazone and buffer.

17. Reagent as claimed in claim 9 wherein the system for the determination of a substrate and the ascorbate oxidase are impregnated with an absorbent carrier material.

18. Reagent as claimed in claim 17 comprising an absorbent carrier impregnated with glucose oxidase, peroxidase, ascorbate oxidase, a 9-($\gamma$-dimethylaminopropyl)-6-chloro-3-aminocarbazole salt and buffer.

19. Reagent as claimed in claim 18 comprising an absorbent carrier impregnated with an ethylenediamine-tetraacetic acid salt, dioctyl sodium sulphosuccinate, 2,5-dimethylhexane-2,5-dihydroperoxide, phosphoric acid trimorpholide, ascorbate oxidase, 3,3',5,5'-tetramethylbenzidine, phenanthridine and buffer.

20. Reagent as claimed in claim 17 wherein the aborbent carrier is a paper.

21. Reagent as claimed in claim 9 wherein the ascorbate oxidase is impregnated into a water-soluble sheet of carrier material and the system for the determination of a substrate is impregnated into a water-insoluble sheet of absorbent carrier material, the water-soluble and the water-insoluble carrier materials being placed on top of one another.

22. Reagent as claimed in claim 17 comprising ascorbate oxidase, gum guaiac and buffer.

* * * * *